United States Patent [19]

Carlier et al.

[11] Patent Number: 4,820,702
[45] Date of Patent: Apr. 11, 1989

[54] NEW SUBSTITUTED PIPERIDINE OR AZEPINE COMPOUNDS WHICH HAVE USEFUL CALCIUM-ANTAGONISTIC ACTIVITY

[75] Inventors: Patrick Carlier, Chatel-Guyon; Jacques A. Simond, Les-Martres-de-Veyre; André J. Monteil, Chatel-Guyon, all of France

[73] Assignee: Riom Laboratories C.E.R.M., Riom, France

[21] Appl. No.: 136,583

[22] Filed: Dec. 22, 1987

[30] Foreign Application Priority Data

Dec. 23, 1986 [FR] France ................. 86 18082

[51] Int. Cl.⁴ .................. A61K 31/445; C07D 211/40
[52] U.S. Cl. .................... 514/212; 514/327; 514/315; 540/604; 546/216; 546/242
[58] Field of Search ............... 546/216, 242; 540/604; 514/212, 315, 327

[56] References Cited

U.S. PATENT DOCUMENTS

| | | | |
|---|---|---|---|
| 2,976,146 | 3/1961 | Biel | 546/216 |
| 3,081,309 | 3/1963 | Prost | 546/216 |
| 3,579,512 | 3/1971 | Kuhnis et al. | 546/225 |
| 3,681,501 | 8/1972 | Kuhnis et al. | 514/330 |
| 3,687,955 | 8/1972 | Cerbati et al. | 546/129 |
| 3,776,908 | 12/1973 | Cerbati et al. | 544/171 |

Primary Examiner—Mary C. Lee
Assistant Examiner—Zinna Northington
Attorney, Agent, or Firm—William M. Blackstone

[57] ABSTRACT

Compounds of formula:

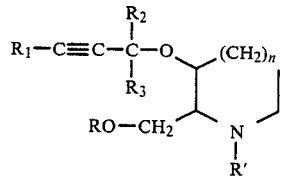

in which R and R' denote an alkyl radical having 1 to 7 carbon atoms; $R_1$ denotes hydrogen or an alkyl radical having 1 to 7 carbon atoms; and $R_2$ and $R_3$ denote, separately, an alkyl radical having 1 to 7 carbon atoms or a phenyl radical, or, together with the carbon atom to which they are attached, a cycloalkyl radical having at most 7 carbon atoms; n may assume the values 2 or 3; and their pharmaceutically acceptable salts.

Application as a cardiovascular medicinal product.

5 Claims, No Drawings

NEW SUBSTITUTED PIPERIDINE OR AZEPINE COMPOUNDS WHICH HAVE USEFUL CALCIUM-ANTAGONISTIC ACTIVITY

The present invention relates to new substituted piperidines or azepines, the preparation thereof and their application in therapy.

More precisely, the 1-alkyl-2-alkoxymethyl-3-alkynyloxypiperidines or -azepines of the invention correspond to the following general formula:

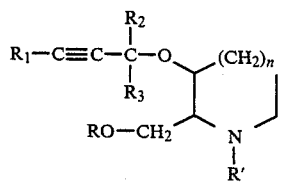

in which R and R' denote an alkyl radical having 1 to 7 carbon atoms; $R_1$ denotes hydrogen or an alkyl radical having 1 to 7 carbon atoms; and $R_2$ and $R_3$ denote, separately, an alkyl radical having 1 to 7 carbon atoms or a phenyl radical, or, together with the carbon atom to which they are attached, a cycloalkyl radical having at most 7 carbon atoms; n may assume the values 2 or 3.

The invention also relates to the salts of the said compounds with pharmaceutically acceptable organic or inorganic acids, such as hydrochloric, fumaric, maleic, citric or succinic acid, these acids being mentioned only by way of illustration and without representing a limitation.

According to a preferred embodiment, the substituents R', $R_1$, $R_2$ or $R_3$ denote a methyl radical.

When $R_2$ and $R_3$ together denote a cycloalkyl radical a preferred embodiment consists of a cyclohexyl radical.

In the definition of the substituent R, the ethyl and isobutyl radicals constitute the preferred embodiments.

Since the compounds of the invention contain asymetric carbon atoms, racemic and/or separate optically active isomers as well as mixtures thereof form part of the invention.

Pharmacological studies showed that the compounds of the invention possessed advantageous properties, enabling them to be applied in human therapy in the treatment of cardiovascular disorders.

The compounds of the invention can be prepared, starting with the 2-(α-hydroxy-β-alkoxyethyl)-pyrrolidine or -piperidine, according to the reaction scheme below:

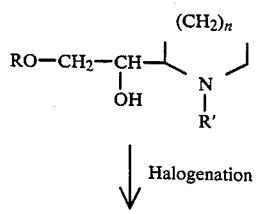

Halogenation

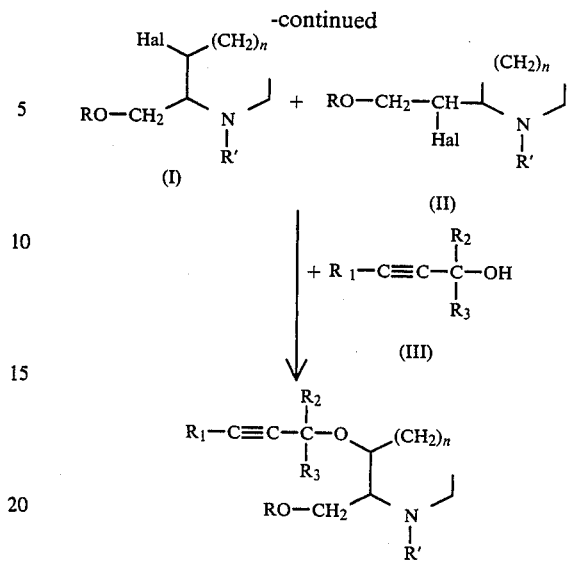

In a first stage, the halogenation of a 2-(α-hydroxy-β-alkoxyethyl) pyrrolidine or -piperidine is performed be means of a customary halogenating agent, such as $SOCl_2$ or $PBr_3$, in a solvent such as chloroform, at a temperature between room temperature and the refluxing temperature of the solvent.

The halogenated derivative formed can have the structure I or the structure II, or alternatively can be a mixture of the two types of structure.

In the first stage, the compound of type I (corresponding to an enlargement of the nitrogen-containing ring) is predominantly obtained when n=2, whereas only compounds of type II are obtained when n=3, the ring enlargement taking place in the second stage.

In the second stage, the product obtained in the previous stage is reacted with an acetylenic alcohol of formula III preferably by phase transfer in the presence of a strong base such as 50–70% sodium hydroxide solution and a catalyst such as benzyltriethylammonium chloride, a solvent such as toluene or methylene chloride being added if the viscosity of the medium requires it.

At the end of this stage, the compounds of the invention are extracted from the reaction mixture by the customary methods (for example by extraction with ether or methylene chloride) and then purified by preparative liquid chromatography.

The examples illustrate in greater detail the preparation of the compounds of the invention.

EXAMPLE 1

1-methyl-2-[(2-methylpropoxy)methyl]-3-{[1-(1-propynyl)cyclohexyl]oxy}piperidine In a first stage, 100 g (0.5 mol) of 1-methyl-2-(α-hydroxy-β-isobutoxyethyl)pyrrolidine were introduced into a reactor containing 1 l of anhydrous chloroform, the mixture was then heated to 50° C. and a solution of 82 ml of thionyl chloride in 80 ml of anhydrous chloroform was introduced dropwise, and the mixture was maintained for 4 hours while being heated to the refluxing point of the solvent.

The solvent was then evaporated off and the residue was taken up with 1 l of 3% strength hydrochloric acid, then washed with methylene chloride, alkalinized with caustic soda solution and then extracted with methylene chloride. After drying over sodium sulphate and evaporation of the solvent, the residue was distilled and 64 g of 1-methyl-2-isobutoxymethyl-3-chloropiperidine were obtained, of boiling point B.p.$_{0.5}$ 92°–93° C.

In the second stage, 22 g of sodium hydroxide, 110 ml of toluene, 2.2 g of benzyltriethylammonium chloride, 22 ml of water and 21 g of 1-(1-propynyl)cyclohexanol were introduced into a reactor, a solution of 22 g of the chlorinated derivative obtained above in 60 ml of toluene was added dropwise and the mixture was heated to 70°–80° C. for 10 hours. After being cooled, the mixture was decanted, the aqueous phase was washed with methylene chloride, and the organic phases were combined, washed with water and dried over sodium sulphate.

After evaporation and distillation, 13.5 g of crude product were obtained, of boiling point B.p.$_{0.5}$ 132°–135° C.

The product obtained was then purified by preparative liquid chromatography on silica gel using a solvent having the following composition: $CH_2Cl_2$, 89.9%; $CH_3OH$, 10%; $NH_4OH$, 0.1%.

6 g of compound of the title were thereby obtained, having an index $n_D^{20} = 1.4850$ and the following elementary analysis:

|  | C % | H % | N % |
|---|---|---|---|
| Theoretical | 74.72 | 10.97 | 4.36 |
| Found | 73.44 | 11.04 | 4.36 |

EXAMPLE 2

1-methyl-2-[(2-methylpropoxy)methyl]-3-[(1-methyl-1-phenyl-2-propynyl)oxy]azepine According to the same method as that described in Example 1, starting with 16 g of 1-methyl-2-(α-hydroxy-β-isobutoxyethyl)piperidine dissolved in 160 ml of anhydrous chloroform and with 16 ml of thionyl chloride in 16 ml of anhydrous chloroform, 9.7 g of 1-methyl-2-(α-chloro-β-isobutoxyethyl)piperidine were obtained after 18 hours' heating under reflux, and this product was used in the crude state in the following step.

In the second step, using for the phase transfer a composition similar to that described in Example 1, 6 g of compound of the title was obtained, in the crude state, starting with the compound of the previous stage and 10.3 g of 3-phenyl-1-butyn-3-ol, the product having the melting point B.p.$_{0.2}$ 160°–165° C.

To purify the product obtained, preparative liquid chromatography was performed on silica gel, using as solvent a mixture of dichloromethane containing increasing amounts of methanol (from 0% to 4%).

2.9 g of purified compound were thereby obtained, having an index $n_D^{20} = 1.5075$ and the following elementary analysis:

|  | C % | H % | N % |
|---|---|---|---|
| Theoretical | 76.92 | 9.68 | 4.07 |
| Found | 76.27 | 9.79 | 4.09 |

EXAMPLE 3

1-methyl-2-(ethoxymethyl)-3-[(1-methyl-1-phenyl-2-propynyl)oxy]piperidine

Working as described in Example 1, in a first stage, by the action of thionyl chloride, 1-methyl-2-ethoxymethyl-3-chloropiperidine was obtained, of boiling point B.p.$_{12}$ 100° C.

By reacting this chlorinated derivative with 3-phenyl-1-butyn-3-ol for 5 hours in the presence of the phase transfer mixture, and then performing a purification by preparative chromatography on silica gel, with the same solvent as for Example 1, the compound of the title was obtained, having the index $n_D^{20} = 1.5150$ and the following elementary analysis:

|  | C % | H % | N % |
|---|---|---|---|
| Theoretical | 75.71 | 9.03 | 4.65 |
| Found | 75.33 | 9.02 | 4.63 |

In the same manner, a number of compounds according to the invention were prepared, the properties of which are summarized in Table I below:

TABLE I

| COMPOUND No. | $R_1$ | $R_2$ | $R_3$ | R | n | $n_D^{20}$ | B.p.$_{mmHg}$ | °C. |
|---|---|---|---|---|---|---|---|---|
| 1 (Example 1) | —$CH_3$ | —$(CH_2)_5$— | $CH_3$<br>\<br>CH—$CH_2$—<br>/<br>$CH_3$ |  | 2 | 1.4852 | B.p.$_{0.5}$ | 132–135 |
| 2 (Example 3) | H | —C$_6$H$_5$ | —$CH_3$ | —$C_2H_5$ | 2 | 1 5150 | B.p.$_{0.1}$ | 134–136 |
| 3 | H | —C$_6$H$_5$ | —$CH_3$ | $CH_3$<br>\<br>CH—$CH_2$—<br>/<br>$CH_3$ | 2 | 1.5090 | B.p.$_1$ | 93 |
| 4 (Example 2) | H | —C$_6$H$_5$ | —$CH_3$ | $CH_3$<br>\<br>CH—$CH_2$—<br>/<br>$CH_3$ | 3 | 1.5075 | B.p.$_{0.2}$ | 160–165 |

TABLE I-continued

| COMPOUND No. | R₁ | R₂ | R₃ | R | n | $n_D^{20}$ | B.p.$_{mmHg}$ | °C. |
|---|---|---|---|---|---|---|---|---|
| 5 | —CH₃ | (CH₂)₅— | | 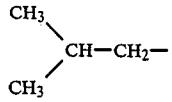 | 3 | 1.4860 | B.p.$_{0.1}$ | 130–138 |

In Table I above, the substituent R' signifies a methyl radical.

The compounds of the invention were shown to possess advantageous antianginal properties, with bradycardic, antitachycardiac and coronary dilatory effects.

The calcium-antagonistic activity was tested according to the technique of Van Rossum (Arch. Int. Pharmacodyn. Ther. 143, 299–330, 1963). To assess the calcium-antagonistic activity at the cardiac level, electrically stimulated rabbit papillary muscle was used (frequency 1.5 Hz; 15 v impulse for 5 ms). For the activity at the vascular level, rabbit aorta cut into a spiral and maintained in a solution devoid of Ca++ and enriched with K+ (6 mg/l of KCl) was used. The measurements were performed 15 minutes after adding the compounds to the solution. The traditional parameters of molecular pharmacology are recorded in Table II.

The test of antianginal activity was assessed by investigating the haemodynamic effects in anaesthetized dogs. The animal is anaesthetized with chloralose (100 mg kg⁻¹ i.v.) and the following parameters are recorded:

heart rate using subcutaneous ECG electrodes connected to a cardiotachometer, the coronary arterial flow using an electromagnetic flow meter, the blood pressure using a Mikro-tip catheter at the level of the aortic arch, the inotropism, assessed by the left maximal dP/dt, by derivation with respect to time of the left intraventricular pressure recorded using a Mikro-tip catheter in the left ventrical, the antitachycardiac action (inhibition of the positive chronotropic effects of isoprenaline).

These parameters are recorded continuously on a Beckman dynograph. The compounds are administered i.v. at a dose of 5 mg kg⁻¹.

The results are expressed as a percentage variation, the duration of action being indicated in brackets, in minutes (Table III).

TABLE II

| COMPOUND No. | CALCIUM-ANTAGONISTIC ACTIVITY | |
|---|---|---|
| | CARDIAC | VASCULAR |
| 1 | 4.8 | 5.6 |
| 2 | 4.5 | 4.9 |
| 3 | 4.6 | 5.6 |
| 4 | 5.4 | 5.6 |
| 5 | 4.7 | 4.9 |

TABLE III

| COMPOUND NO. | HAEMODYNAMIC ACTIVITY | | | | |
|---|---|---|---|---|---|
| | HEART RATE | CORONARY FLOW | HYPOTENSION | INOTROPISM | ANTITACHYCARDIA |
| 1 | −17 (>40) | +124 (10) | −32 (5) | −13 (3) | 0 |
| 2 | −12 (>40) | +114 (4) | −9 (2) | −19 (>39) | −27 (17) |
| 3 | −24 (>40) | +44 (4) | −55 (7) | −61 (>40) | −30 (17) |
| 4 | −30 (>40) | +64 (2) | −50 (5) | −32 (>40) | −15 (17) |
| 5 | −41 (>40) | +25 (2) | −58 (4) | −50 (23) | 0 |

These results show that the compounds of the invention have calcium-antagonistic activity on both heart muscle and vascular muscle, the compounds nos. 1 and 3 being those which show the strongest activity.

As regards the haemodynamic effects, all these compounds are capable of being, to differing extents, antianginals and/or anti-ischaemics as a result of their bradycardic, coronary dilatory and antitachycardiac activities. Their action on the bloodpressure also makes it possible to envisage applying them as an antihypertensive. The compound no. 1 is that which shows the most favourable parameters.

The toxicity was observed orally in mice, and no death was observed up to 500 mg kg⁻¹.

This combination of pharmacological properties enables the compounds of the invention to be applied to human therapy as a medicinal product for the treatment of cardiovascular disorders such as angina pectoris, ischaemia or hypertension.

The compounds of the invention may be administered enterally or parenterally at daily dosage between 0.5 mg and 10 mg per kg body weight depending on the method of administration.

For the treatment of human beings a daily dosage of 50 up to 500 mg is preferred.

Mixed with suitable auxiliaries the compounds of the invention or salts thereof may be compressed into solid dosage units such as pills, tablets coated tablets, etc. or may be processed into capsules. By means of suitable liquids. the compounds may also be applied as an injection, or oral preparation in form of solutions, suspensions or emulsions.

What is claimed is:

1. A compound of the formula:

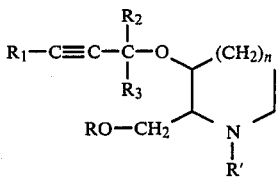

in which R and R' denote an alkyl radical having 1 to 7 carbon atoms; $R_1$ denotes hydrogen or an alkyl radical having 1 to 7 carbon atoms; and $R_2$ and $R_3$ denote, separately, an alkyl radical having 1 to 7 carbon atoms or a phenyl radical, or, together with the carbon atom to which they are attached, a cycloalkyl radical having at most 7 carbon atoms; n may assume the values 2 or 3; or a salt thereof.

2. A compound according to claim 1, wherein the substituents R', $R_1$, $R_2$ or $R_3$ denote the methyl radical.

3. A compound according to claim 1, wherein $R_2$ and $R_3$ together denote a cyclohexyl radical.

4. A compound according to claim 1, wherein R denotes an ethyl radical or an isobutyl radical.

5. Pharmaceutical composition comprising an effective amount of a compound according to claim 1 for providing calcium-antagonistic activity and an inert carrier.

* * * * *